US010167255B2

(12) United States Patent
List et al.

(10) Patent No.: US 10,167,255 B2
(45) Date of Patent: Jan. 1, 2019

(54) PROCESS FOR PREPARING AMINES

(71) Applicant: STUDIENGESELLSCHAFT KOHLE MBH, Mülheim an der Ruhr (DE)

(72) Inventors: Benjamin List, Mülheim an der Ruhr (DE); Denis Alexandrovich Chusov, Moscow (RU)

(73) Assignee: STUDIENGESELLSCHAFT KOHLE MBH, Muelheim an der Ruhr (DE)

( * ) Notice: Subject to any disclaimer, the term of this patent is extended or adjusted under 35 U.S.C. 154(b) by 0 days.

(21) Appl. No.: 14/651,066

(22) PCT Filed: Dec. 10, 2013

(86) PCT No.: PCT/EP2013/076093
§ 371 (c)(1),
(2) Date: Jun. 10, 2015

(87) PCT Pub. No.: WO2014/090806
PCT Pub. Date: Jun. 19, 2014

(65) Prior Publication Data
US 2015/0315140 A1 Nov. 5, 2015

(30) Foreign Application Priority Data
Dec. 11, 2012 (EP) ..................... 12196518

(51) Int. Cl.
*C07D 207/04* (2006.01)
*C07D 295/023* (2006.01)
*C07D 295/03* (2006.01)
*C07C 209/78* (2006.01)
*C07C 209/28* (2006.01)
*C07C 213/08* (2006.01)

(52) U.S. Cl.
CPC .......... *C07D 207/04* (2013.01); *C07C 209/28* (2013.01); *C07C 209/78* (2013.01); *C07C 213/08* (2013.01); *C07D 295/023* (2013.01); *C07D 295/03* (2013.01)

(58) Field of Classification Search
CPC ... C07C 209/28; C07C 213/08; C07C 211/27; C07C 217/84; C07C 209/78; C07D 207/04; C07D 295/023; C07D 295/03
See application file for complete search history.

(56) References Cited

U.S. PATENT DOCUMENTS

| 3,091,641 | A | | 5/1963 | Sweeney | |
|---|---|---|---|---|---|
| 3,947,458 | A | * | 3/1976 | Iqbal | C07C 209/60 546/184 |
| 4,831,159 | A | * | 5/1989 | Lin | C07C 209/62 548/551 |
| 6,025,524 | A | * | 2/2000 | Herwig | C07C 209/60 564/467 |
| 7,220,884 | B2 | * | 5/2007 | Briggs | C07C 33/30 544/178 |
| 2009/0227801 | A1 | * | 9/2009 | Ahlers | B01J 31/1855 548/101 |

FOREIGN PATENT DOCUMENTS

| DE | 926 847 C | 4/1955 |
|---|---|---|
| DE | 10012251 A1 * | 12/2000 |
| JP | S 41-125331 A | 11/1976 |
| JP | S 55-43008 A | 3/1980 |

OTHER PUBLICATIONS

Chan Sik Cho (J. Heterocyclic Chem., 34, 1371 (1977).*
Mark'o (Journal of Organometallic Chemistry vol. 81, Issue 3, Nov. 26, 1974, pp. 411-414).*
Rische et al.(Tetrahedron 54 (1998) 2723-2742).*
Fikret Koc (Tetrahedron 60 (2004) 8465-8476).*
Watanabe (Tetrahedron Letters No. 15, pp. 1289-1290, (1978)).*
Cho et al; "Palladium-Catalyzed Synthesis of 3-(Alkylamino)isoindolin-1-ones by Carbonylative Cyclization of 2-Bromobenzaldehyde with Primary Amines"; J. Heterocyclic Chem., vol. 34, pp. 1371-1374 (1997).
Rische et al; "Selective One-Pot Synthesis of Symmetrically and Unsymmetrically Substituted Amines via Rhodium Catalysed Multiple Alkylations of Ammonia or Primary Amines under Hydroformylation Conditions"; Tetrhedron 54 pp. 2723-2742 (1998).
Cho et al; "An Unprecedented Ruthenium-Catalyzed Reductive Amination of Aldehydes with Tertiary Amines"; Bull. Korean Chem. Soc., vol. 23, No. 1, pp. 23-24 (2002).
International Search Report in corresponding application PCT/EP2013/076093 dated Apr. 22, 2014.
"Yield (chemistry)," en.Wikipedia.org, Dec. 28, 2017.
English translation of Office Action issued by Japanese Patent Office dated Jul. 14, 2017, in connection with Japanese Patent Application No. 2015-546976.

* cited by examiner

Primary Examiner — Valerie Rodriguez-Garcia
(74) Attorney, Agent, or Firm — Norris McLaughlin, P.A.

(57) ABSTRACT

The present invention refers to a process for preparing amines comprising reacting a compound of the formula $R^1$—CO—$R^2$ comprising a carbonyl moiety with a amine compound of the formula $HNR^3R^4$ and carbon monoxide in the presence of a catalyst.

5 Claims, No Drawings

PROCESS FOR PREPARING AMINES

This application is a 371 of International Patent Application No. PCT/EP2013/076093, filed Dec. 10, 2013, which claims foreign priority benefit under 35 U.S.C. § 119 of the European Patent Application No. 12196518.0, filed Dec. 11, 2012, the disclosures of which patent applications are incorporated herein by reference.

The present invention relates to a novel organic reaction and to methods for making and using such reaction products. In more detail, the present invention relates to a novel reaction for reductive amination and to methods for making further products from the reaction products without the need of an external hydrogen source.

The reductive amination of carbonyl compounds is key for the production of amines and without exception, requires a source of hydrogen, most commonly hydrogen gas ($H_2$) itself. However, while hydrogen is inexpensive and used on an industrial scale, it has a wide explosive range with air and can cause massive detonations.

In addition, most hydrogen today is produced from fossil materials, such as natural gas. The main process to accomplish this is by steam methane reforming (SMR) process comprising two steps. The first step involves reacting methane ($CH_4$) with steam at 750-800° C. to produce $H_2$ and CO. The CO-byproduct is then channeled into the second step, known as the water gas shift (WGS) reaction, in which it reacts with more steam over a catalyst to form additional $H_2$ and carbon dioxide ($CO_2$). This process itself occurs in two stages, consisting of a high temperature shift at 350° C. and a low temperature shift at 190-210° C. In the final step, the hydrogen has to be separated from carbon dioxide, methane, unreacted carbon monoxide, and water. Once purified, the resulting supply of hydrogen is utilized in a myriad of applications including reductive aminations.

Other hydrogen sources can be less economic and expensive or unstable to moisture and air.

Amines are a very useful and irreplaceable class of compounds. They are employed not only in the industry and laboratory as products (such as pharmaceuticals, dyes, gas treatment, etc.) but also as reagents and catalysts. Accordingly, there is a need for a simple and efficient process for preparing amines.

The inventors have investigated several approaches for preparing amines. One of the most important methods to synthesize amines is via the reduction of imines. As a more direct and economical approach, the reductive amination of carbonyl compounds with amines avoids the separate step of imine formation. This method therefore requires fewer purification steps and generates less solvent waste.

The inventors studied several potential homogenous and heterogeneous catalyst systems and considered that, in the context of industrial applications, using CO directly as a reductant could offer distinct advantages as three steps including heating up to 350° C. and three different catalysts as used in the state of art would potentially be converted into a single operation using only a single catalyst.

The reaction of carbon monoxide with amine-compounds is known in the prior art, for example from Chan Sik Cho in Journal of Heterocyclic Chemistry, 1997, Pages 1371-1374. However, said process is a well known carbonylation reaction of an aryl halide with CO, which is combined with further deoxo-bisubstitution reaction of the aldehyde, thus forming an indolinone compound. In said reaction, no reduction is taking place, and the process is therefore not a reductive amination as in the present invention.

The inventors also tested other homogeneous and heterogeneous metal catalysts, and finally, the inventors identified a rhodium salt such as rhodium acetate as a particularly efficient catalyst for the reductive amination of an aldehyde such as benzaldehyde with p-anisidine in the presence of carbon monoxide furnishing N-benzyl-4-methoxyaniline. Upon solvent screening, it was found that the reaction catalyzed by rhodium acetate proceeded efficiently in a variety of solvents, with highest reaction rate reached in THF. rhodium sources such as $Rh(PPh_3)_3Cl$, $Rh_6(CO)_{16}$, $[Rh(CO)_2Cl]_2$, $[Rh(COD)Cl]_2$, $HRh(PPh_3)_4$, heterogeneous rhodium and ruthenium but all of them showed varying catalytic activities.

Thus, the present invention relates to a novel reaction of reductive amination and to methods for making any further products from these. The reaction is depicted below:

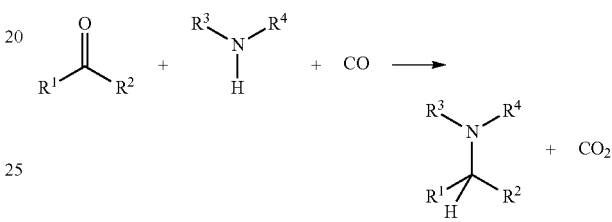

Therefore, the present invention is directed to a process for preparing amines where a compound comprising a carbonyl moiety of the formula $R^1$—CO—$R^2$ is reacted with a compound of the formula $HNR^3R^4$ and carbon monoxide in the presence of a catalyst. The catalyst can be particularly selected from heterogeneous and/or homogeneous metal catalysts selected from Pt, Pd, Ir, Rh, Ru, Os, Mo, Ni, Cr, V, Cu, Mn, Zn, Fe, sulfur, selenium and their catalytically active compounds. The reaction can be carried out in a solvent or solvent-free.

In the above formulae, $R^1$ and $R^2$ are each independently hydrogen or a hydrocarbon group which may be the same of different and may be selected each from $C_1$ to $C_{20}$ straight chain, branched chain or cyclic aliphatic hydrocarbons, optionally including hetero atoms and/or optionally having one or more unsaturated bonds, such as $C_1$-$C_{20}$-alkyl, $C_2$-$C_{20}$-alkenyl or $C_2$-$C_{20}$-alkynyl, $C_3$-$C_8$-heterocycloalkyl, $C_6$ to $C_{20}$ aromatic hydrocarbon or partially arene-hydrogenated forms such as aryl, aryl-($C_1$-$C_6$)-alkyl, heteroaryl-($C_1$-$C_6$)-alkyl, each hydrocarbon substituent optionally being substituted by one or more groups selected from $C_1$ to $C_{20}$ straight chain, branched chain or cyclic aliphatic hydrocarbons, optionally including hetero atoms and/or optionally having one or more unsaturated bonds such as $C_1$-$C_{20}$-alkyl, $C_2$-$C_{20}$-alkenyl or $C_2$-$C_{20}$-alkynyl, or $C_6$ to $C_{20}$ aromatic hydrocarbon or partially arene-hydrogenated forms such as aryl, aryl-($C_1$-$C_6$)-alkyl, heteroaryl-($C_1$-$C_6$)-alkyl or heterosubstituents, wherein at least one of $R^1$ and $R^2$ is not hydrogen, or $R^1$ and $R^2$ form a cycloaliphatic or heterocycloaliphatic ring structure having 4 to 10 ring atoms optionally including unsaturated bond(s), each ring structure optionally being substituted by one or more substituents selected from heterosubstituents, $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkynyl, $C_3$-$C_8$-heterocycloalkyl or $C_6$ to $C_{20}$ aromatic hydrocarbon such as aryl, aryl-($C_1$-$C_6$)-alkyl, heteroaryl-($C_1$-$C_6$)-alkyl, each hydrocarbon optionally being substituted by one or more heterosubstituents, and $R^3$ and $R^4$ are each independently hydrogen or a hydrocarbon group which may be the same of different and may be selected each from $C_1$ to $C_{20}$ straight chain, branched chain or cyclic aliphatic hydrocarbons, optionally including hetero atoms and/or optionally having one or more unsaturated bonds such as $C_1$-$C_{20}$-alkyl, $C_2$-$C_{20}$-alkenyl or $C_2$-$C_{20}$-alkynyl, $C_3$-$C_8$-heterocycloalkyl or $C_6$ to $C_{20}$ aromatic hydrocarbon or partially arene-hydrogenated forms such as aryl, aryl-($C_1$-$C_6$)-alkyl, heteroaryl-($C_1$-$C_6$)-alkyl, each hydrocarbon substituent optionally being substituted by one or more groups selected from $C_1$ to $C_{20}$ straight chain, branched chain or cyclic aliphatic hydrocarbons, optionally including hetero atoms and/or optionally having one or more unsaturated bonds such as $C_1$-$C_{20}$-alkyl, $C_2$-$C_{20}$-alkenyl or $C_2$-$C_{20}$-alkynyl, or $C_6$ to $C_{20}$ aromatic hydrocarbon or partially arene-hydrogenated forms such as aryl, aryl-($C_1$-$C_6$)-alkyl, heteroaryl-($C_1$-$C_6$)-alkyl or heterosubstituents, wherein at least one of $R^3$ and $R^4$ is not hydrogen, or $R^3$ and $R^4$ form a cycloaliphatic or heterocycloaliphatic ring structure having 4 to 10 ring atoms optionally including unsaturated bond(s), each ring structure optionally being substituted by one or more substituents selected from heterosubstituents, $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkynyl, $C_3$-$C_8$-heterocycloalkyl or $C_6$ to $C_{20}$ aromatic hydrocarbon such as aryl, aryl-($C_1$-$C_6$)-alkyl, heteroaryl-($C_1$-$C_6$)-alkyl, each hydrocarbon optionally being substituted by one or more heterosubstituents.

In the above formulae, $R^1$ and $R^2$ may in particular be each independently hydrogen or a substituent selected from the group consisting of $C_1$-$C_{20}$ alkyl, $C_2$-$C_{20}$ alkenyl, $C_2$-$C_{20}$ alkynyl, aryl, preferably $C_6$ to $C_{14}$ aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthiol, arylthiol, $C_1$-$C_{20}$ alkylsulfonyl, $C_1$-$C_{20}$ alkylsulfinyl, the substituent optionally substituted with one or more moieties selected from the group consisting of $C_1$-$C_{10}$ alkyl, $C_1$-$C_{10}$ alkoxy, aryl, preferably $C_6$ to $C_{14}$ aryl, and one or more functional groups selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen, wherein at least one of $R^1$ and $R^2$ is not hydrogen, and $R^3$ and $R^4$ may each independently be hydrogen or a substituent selected from the group consisting of $C_1$-$C_{20}$ alkyl, $C_2$-$C_{20}$ alkenyl, $C_2$-$C_{20}$ alkynyl, aryl, preferably $C_6$ to $C_{14}$ aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthiol, arylthiol, $C_1$-$C_{20}$ alkylsulfonyl, $C_1$-$C_{20}$ alkylsulfinyl, the substituent optionally substituted with one or more moieties selected from the group consisting of $C_1$-$C_{10}$ alkyl, $C_1$-$C_{10}$ alkoxy, aryl, preferably $C_6$ to $C_{14}$ aryl, and one or more functional groups selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen, wherein at least one of $R^3$ and $R^4$ is not hydrogen.

A heterosubstituent as defined above according to the invention can be selected from, =O, OH, F, Cl, Br, I, CN, $NO_2$, $SO_3H$, a monohalogenomethyl group, a dihalogenomethyl group, a trihalogenomethyl group, $CF(CF3)_2$, $SF_5$, amine bound through N atom, —O-alkyl (alkoxy), —O-aryl, —O—$SiR^S_3$, S—$R^S$, S(O)—$R^S$, S(O)$_2$—$R^S$, COOH, $CO_2$—$R^S$, amide, bound through C or N atom, formyl group, C(O)—$R^S$, COOM, where M may be a metal such as Na or K. $R^S_3$ may be, independently from each other, the same or different and may be each an aliphatic, heteroaliphatic, aromatic or heteroaromatic group, each optionally being further substituted by one or more heterosubstituents, aliphatic, heteroaliphatic, aromatic or heteroaromatic groups.

Aliphatic hydrocarbons including alkyl, alkenyl and alkynyl may comprise straight-chain, branched and cyclic hydrocarbons.

Heteroaliphatic is a hydrocarbon having 1 to 20 carbon atoms including alkyl, alkenyl and alkynyl which may comprise straight-chain, branched and cyclic hydrocarbons with one or more carbon atoms replaced or substituted with a heteroatom.

In more detail, $C_1$-$C_{20}$-Alkyl can be straight chain or branched and has 1, 2, 3, 4, 5, 6, 7, 8, 9, 10, 11, 12, 13, 14, 15, 16, 17, 18, 19 or 20 carbon atoms. Alkyl might be $C_1$-$C_6$-alkyl, in particular methyl, ethyl, propyl, isopropyl, butyl, isobutyl, sec-butyl or tert-butyl, likewise pentyl, 1-, 2- or 3-methylpropyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. Substituted alkyl groups are trifluoromethyl, pentafluoroethyl and 1,1,1-trifluoroethyl.

Cycloalkyl might be cyclopropyl, cyclobutyl, cyclopentyl, cyclohexyl or cycloheptyl. Alkenyl might be $C_2$-$C_{20}$ alkenyl. Alkynyl might be $C_2$-$C_{20}$ alkynyl.

Halogen is F, Cl, Br or I.

Alkoxy is preferably $C_2$-$C_{10}$ alkoxy such as methoxy, ethoxy, propoxy, tert-butoxy etc.

$C_3$-$C_8$-Heterocycloalkyl having one or more heteroatoms selected from among N, O and S is preferably 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl.

Optionally substituted means unsubstituted or monosubstituted, disubstituted, trisubstituted, tetrasubstituted, pentasubstituted, or even further substituted for each hydrogen on the hydrocarbon.

Aryl might be phenyl, naphthyl or biphenyl.

Arylalkyl might be benzyl.

Heteroaryl having one or more heteroatoms selected from among N, O and S is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, also preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-Indolyl, 4- or 5-isoindolyl, 1-, 2-, 4- or 5-benz-imidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, also preferably 1,3-benzodioxol-5-yl, 1,4-benzodioxan-6-yl, 2,1,3-benzothiadiazol-4- or -5-yl or 2,1,3-benzoxadiazol-5-yl.

The reducing agent is carbon monoxide supplied to the reaction chamber as gas which may content other gases as impurities such as nitrogen, methane, hydrogen, oxygen, carbon dioxide, water, chlorine, argon, helium, neon, xenon or others up to a content of 90%.b.w. referred to the complete gas mixture.

The inventive reaction is generally carried out at a reaction pressure of 1 to 200 bar, preferably 50 to 150 and more preferably 80 to 120 bar.

Depending on the solvent, the inventive reaction is generally carried out at an elevated temperature between 50° to 350° C., preferably 80 to 160° C. and for a reaction time of 2 to 20 hours, preferably 4 to 15 hours.

The reaction may occur either in the presence or absence of any solvent and may optionally include formulation auxiliaries. Known auxiliaries include antistatics, antioxidants, adhesion promoters, viscosity-increasing agents, light stabilizers, plasticizers, dyes, pigment, fillers, reinforcing fibers, lubricants and demolding enhancers.

The solvent used in the inventive process may be selected from aliphatic, cycloaliphatic or aromatic solvents, esters, ethers or mixtures thereof such as hexan, benzene, toluene, aliphatic alcohols such as THF, MeOH, DMSO, AcOH, ethyl acetate or diethyl ether amongst which THF is preferred.

As a catalyst, any metal catalyst can be used and can be particularly selected from heterogeneous and/or homogeneous metal catalysts selected from Pt, Pd, Ir, Rh, Ru, Os, Mo, Ni, Cr, V, Cu, Mn, Zn, Fe, sulfur, selenium and their catalytically active compounds. Rhodium compounds such as rhodium salts like rhodium acetate, $Rh(PPh_3)_3Cl$, $Rh_6(CO)_{16}$, $[Rh(CO)_2Cl]_2$, $[Rh(COD)Cl]_2$, $HRh(PPh_3)_4$ can be advantageously used in the inventive process amongst which rhodium acetate is most promising. The catalyst can be used in catalytic amounts of 0.1 to 5.0 mol-%, related to the molar ratio of the reactants.

As explained above, the present invention generally relates to reductive amination of carbonyl compounds with carbon monoxide and is further illustrated by the following examples.

EXAMPLE 1

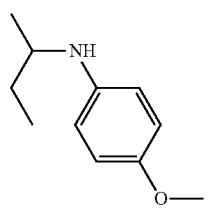

(1)

0.2 mg of $Rh_2(OAc)_4$ was put. Then 27.6 mg of p-anisidine were added. The reaction vial was evacuated and carbon monoxide was added. 0.1 mL of THF (3.7 ppm of water) was added. 20 μL of 2-butanone was added. Autoclave was degassed after which carbon monoxide was added. A CO-pressure of 20 bar was established. The autoclave was heated up to 120° C. After 4 h, the reaction mixture was cooled down to room temperature and the pressure was released. The product was isolated in quantitative yield.

1H NMR (500 MHz, $CDCl_3$) ppm 6.79 (d, J=8.9 Hz, 2H), 6.57 (d, J=8.9 Hz, 2H), 3.75 (s, 3H), 3.38-3.28 (m, 1H), 3.18 (br s, 1H), 1.55-1.67 (m, 1H), 1.40-1.51 (m, 1H), 1.16 (d, J=6.3 Hz, 3H), 0.96 (t, J=7.4 Hz, 3H)

13C NMR (125 MHz, $CDCl_3$) ppm 10.3, 20.1, 29.5, 50.7, 55.7, 114.6, 114.8, 141.9, 151.7

EXAMPLE 2

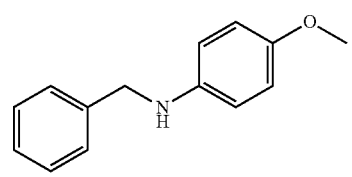

(2)

8.8 mg (0.2 mol %) of $Rh_2(OAc)_4$ were put into a 36 ml autoclave. Then 1.21 g of p-anisidine was added. The autoclave was degassed and carbon monoxide was added. 2 mL of THF were added. 1 mL of benzaldehyde was added. The pressure of CO was 20 bar. The autoclave was heated to 120° C. After 6 h, the reaction mixture was cooled down to room temperature and the pressure was released. The product was isolated in 97% yield.

1H NMR (500 MHz, $CDCl_3$) ppm 7.35-7.45 (m, 4H), 7.31 (t, J=7.0 Hz, 1H), 6.82 (d, J=8.9 Hz, 2H), 6.64 (d, J=8.9 Hz, 2H), 4.32 (s, 2H), 3.78 (s, 3H), 3.70 (br s, 1H). 13C NMR (125 MHz, $CDCl_3$) ppm 49.1, 55.7, 114.0, 114.8, 127.1, 127.5, 128.5, 139.6, 142.4, 152.1

EXAMPLE 3

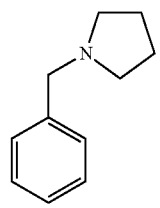

(3)

0.31 mg (0.21 mol %) of $Rh_2(OAc)_4$ was put. Then 28 μL (100 mol %) of pyrrolidine were added. 0.2 mL of THF (18.1 ppm of water) was added. 35 μL of benzaldehyde were added. The pressure of CO was 20 bar. The autoclave was heated to 120° C. After 4 h, the reaction mixture was cooled down to room temperature and the pressure was released. 85% yield.

1H NMR (500 MHz, $CDCl_3$) ppm 7.20-7.45 (m, 5H), 3.66 (s, 2H), 2.50-2.60 (m, 4H), 1.75-1.87 (m, 4H).

13C NMR (125 MHz, CDCl$_3$) ppm 23.4, 54.1, 60.7, 126.8, 128.1, 128.8, 139.3

EXAMPLE 4

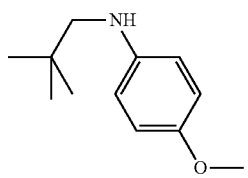
(4)

0.44 mg of Rh$_2$(OAc)$_4$ was put. Then 56.9 mg (100 mol %) of p-anisidine were added. 0.1 mL of THF (19.7 ppm of water) was added. 50 µL of pivaldehyde were added. The pressure of CO was 20 bar. The autoclave was heated to 120° C. After 4 h, the reaction mixture was cooled down to room temperature and the pressure was released. Quantitative yield.

1H NMR (500 MHz, CDCl$_3$) ppm 6.82 (d, J=8.9 Hz, 2H), 6.63 (d, J=8.9 Hz, 2H), 3.77 (s, 3H), 3.40 (br s, 1H), 2.88 (s, 2H), 1.03 (s, 9H)

13C NMR (125 MHz, CDCl$_3$) ppm 27.6, 31.7, 55.7, 59.9, 113.8, 114.8, 143.4, 151.7

EXAMPLE 5

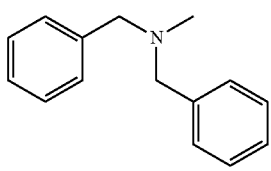
(5)

0.40 mg of Rh$_2$(OAc)$_4$ was put. Then 21 µL of N-methyl-N-benzylamine were added. 0.1 mL of THF (5.7 ppm of water) was added. 18 µL of benzaldehyde were added. The pressure of CO was 20 bar. The autoclave was heated to 140° C. After 12 h, the reaction mixture was cooled down to room temperature and the pressure was released. 93% yield.

1H NMR (500 MHz, CDCl$_3$) ppm 7.10-7.33 (m, 10H), 3.44 (s, 4H), 2.10 (s, 3H).

13C NMR (125 MHz, CDCl$_3$) ppm 42.2, 61.8, 126.9, 128.2, 128.9, 139.2

EXAMPLE 6

(6)

23 mg of 10% Rh/C was put. Then 40 µL of aniline were added. 0.1 mL of THF (21.3 ppm of water) was added. 44 µL of benzaldehyde were added. The pressure of CO was 100 bar. The autoclave was heated to 140° C. After 42 h, the reaction mixture was cooled down to room temperature and the pressure was released. 50% yield.

1H NMR (500 MHz, CDCl$_3$) ppm 7.26-7.44 (m, 5H), 7.17-7.22 (m, 2H), 6.72-6.78 (m, 1H), 6.63-6.79 (m, 2H), 4.35 (s, 2H).

13C NMR (125 MHz, CDCl$_3$) ppm 48.2, 112.8, 117.5, 127.1, 127.4, 128.5, 129.2, 139.4, 148.1

EXAMPLE 7

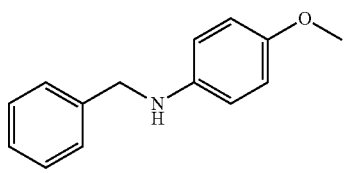
(2)

1.28 mg of Ru$_3$(CO)$_{12}$ were put into a 36 ml autoclave. Then 27.1 mg of p-anisidine was added. The autoclave was degassed and carbon monoxide was added. 0.15 mL of THF (11.0 ppm of water) were added. 20 µL of benzaldehyde was added. The pressure of CO was 95 bar. The autoclave was heated to 100° C. After 6 h, the reaction mixture was cooled down to room temperature and the pressure was released. The product was isolated in 2% yield.

1H NMR (500 MHz, CDCl$_3$) ppm 7.35-7.45 (m, 4H), 7.31 (t, J=7.0 Hz, 1H), 6.82 (d, J=8.9 Hz, 2H), 6.64 (d, J=8.9 Hz, 2H), 4.32 (s, 2H), 3.78 (s, 3H), 3.70 (br s, 1H). 13C NMR (125 MHz, CDCl$_3$) ppm 49.1, 55.7, 114.0, 114.8, 127.1, 127.5, 128.5, 139.6, 142.4, 152.1

As shown above, the present invention provides a simple and efficient process for preparing amines in a direct way by making use of carbon monoxide as reductant. This novel inventive process has safety advantages and shows to be economically viable. Thus, the inventors found an efficient, robust, and general catalytic reductive amination that does not require an external hydrogen source but rather utilizes the existing hydrogen atoms of the substrates and carbon monoxide (CO) as the terminal reductant.

In addition to carbon monoxide being a very useful C-1 building block and known to act as a reductant, mostly proceeding via the water gas shift reaction, the present inventors have shown that carbon monoxide can be also used as a reductant in reductive amination without any external hydrogen source which process being entirely unknown.

The invention claimed is:
1. A process for preparing an amine of formula I comprising reductive amination of a carbonyl compound of the formula II with an amine compound of the formula III and carbon monoxide as reductant in the presence of a catalyst and without introducing hydrogen (H$_2$) from an external hydrogen source to yield said amine of formula I:

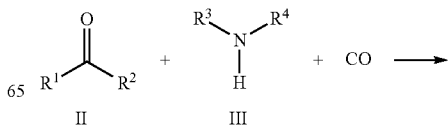

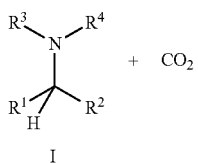

$$\text{I} \quad + \quad CO_2$$

wherein:

R[1] and R[2] are each independently hydrogen or a substituent selected from the group consisting of $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthiol, arylthiol, $C_1$-$C_{20}$ alkylsulfonyl, and $C_1$-$C_{20}$ alkylsulfinyl, each of which is optionally substituted with one or more moieties selected from the group consisting of $C_1$-$C_{10}$ alkyl, $C_1$-$C_{10}$ alkoxy, aryl, and one or more functional groups selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen, wherein at least one of R[1] and R[2] is not hydrogen; and R[3] and R[4] are each independently hydrogen or a substituent selected from the group consisting of $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthiol, arylthiol, $C_1$-$C_{20}$ alkylsulfonyl, and $C_1$-$C_{20}$ alkylsulfinyl, each of which is optionally substituted with one or more moieties selected from the group consisting of $C_1$-$C_{10}$ alkyl, $C_1$-$C_{10}$ alkoxy, aryl, and one or more functional groups selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen, wherein at least one of R[3] and R[4] is not hydrogen.

2. The process according to claim 1, wherein the reaction is carried out in a solvent, selected from aliphatic, cycloaliphatic or aromatic solvents, esters, ethers or mixtures thereof.

3. The process according to claim 1, wherein the reaction is carried out at a reaction pressure of 1 to 200 bar.

4. The process according to claim 1, wherein the reaction is carried out at an elevated temperature between 50° to 350° C.

5. The process according to claim 1, wherein the amine of formula I is obtained in a yield of at least 93%.

* * * * *